(12) United States Patent
Carter et al.

(10) Patent No.: US 9,636,436 B2
(45) Date of Patent: May 2, 2017

(54) COMPOSITIONS OF AND METHODS FOR CANCELLOUS BONE MATRIX

(71) Applicant: THERACELL, INC., Northridge, CA (US)

(72) Inventors: Andrew J. Carter, Stow, MA (US); Nelson L. Scarborough, Andover, MA (US); Bradley Patt, Northridge, CA (US)

(73) Assignee: THERACELL, INC., Northridge, CA (US)

( * ) Notice: Subject to any disclaimer, the term of this patent is extended or adjusted under 35 U.S.C. 154(b) by 0 days.

(21) Appl. No.: 14/776,565

(22) PCT Filed: Mar. 12, 2014

(86) PCT No.: PCT/US2014/024961
§ 371 (c)(1),
(2) Date: Sep. 14, 2015

(87) PCT Pub. No.: WO2014/151091
PCT Pub. Date: Sep. 25, 2014

(65) Prior Publication Data
US 2016/0038639 A1    Feb. 11, 2016

Related U.S. Application Data

(60) Provisional application No. 61/801,766, filed on Mar. 15, 2013, provisional application No. 61/814,197, filed on Apr. 19, 2013, provisional application No. 61/877,825, filed on Sep. 13, 2013.

(51) Int. Cl.
*A61L 27/36* (2006.01)
*A61L 27/56* (2006.01)
*A61L 27/40* (2006.01)
(Continued)

(52) U.S. Cl.
CPC ......... *A61L 27/3608* (2013.01); *A61L 27/365* (2013.01); *A61L 27/3683* (2013.01);
(Continued)

(58) Field of Classification Search
None
See application file for complete search history.

(56) References Cited

U.S. PATENT DOCUMENTS 5,298,254 A * 3/1994 Prewett ............... A61B 17/686
                                                                    424/422
5,439,951 A * 8/1995 Glimcher ............. B01J 20/282
                                                                    264/344
(Continued)

FOREIGN PATENT DOCUMENTS

WO    WO 2014/110537 A1    7/2014

OTHER PUBLICATIONS

Australian Examination Report dated Apr. 14, 2016 issued in corresponding AU Application No. 2014235352, 6pp.
(Continued)

*Primary Examiner* — Aradhana Sasan
(74) *Attorney, Agent, or Firm* — Lewis Roca Rothgerber Christie LLP

(57) ABSTRACT

A bone repair composition including a cancellous bone matrix with cortical and/or cancellous bone particles loaded therein; and a kit comprising the cancellous bone matrix and the cortical and/or cancellous bone particles.

12 Claims, 2 Drawing Sheets

(51) Int. Cl.
*A61L 27/38* (2006.01)
*A61L 27/54* (2006.01)
(52) U.S. Cl.
CPC ....... *A61L 27/3691* (2013.01); *A61L 27/3834* (2013.01); *A61L 27/40* (2013.01); *A61L 27/54* (2013.01); *A61L 27/56* (2013.01); *A61L 2300/406* (2013.01); *A61L 2300/416* (2013.01); *A61L 2430/02* (2013.01)

(56) References Cited

U.S. PATENT DOCUMENTS

| | | | | |
|---|---|---|---|---|
| 5,725,579 | A * | 3/1998 | Fages | A61F 2/4644 128/898 |
| 5,910,315 | A * | 6/1999 | Stevenson | A61F 2/4601 424/422 |
| 2003/0050710 | A1 | 3/2003 | Petersen et al. | |
| 2003/0147860 | A1 | 8/2003 | Marchosky | |
| 2008/0058953 | A1 | 3/2008 | Scarborough | |
| 2008/0262633 | A1 | 10/2008 | Williams et al. | |
| 2008/0305145 | A1 * | 12/2008 | Shelby | A61F 2/4644 424/423 |
| 2009/0155378 | A1 | 6/2009 | Behnam et al. | |
| 2009/0226534 | A1 | 9/2009 | Marchosky | |
| 2012/0082704 | A1 | 4/2012 | Phillips et al. | |

OTHER PUBLICATIONS

International Search Report and Written Opinion for corresponding International Application No. PCT/US2014/024961, mailed Sep. 12, 2014, 17pp.

\* cited by examiner

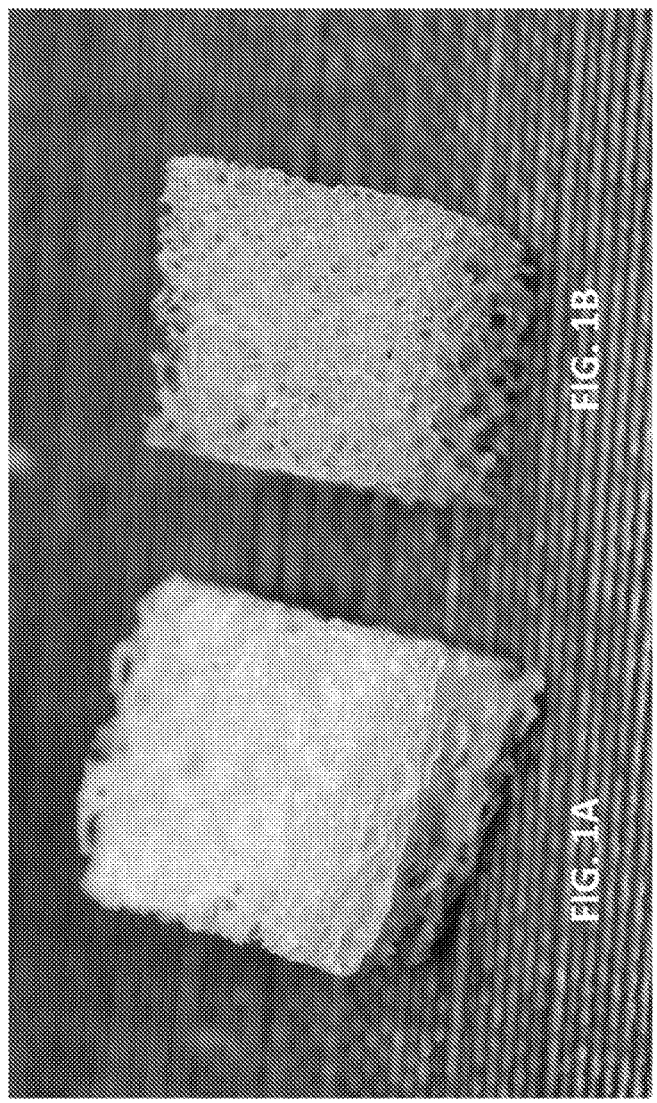

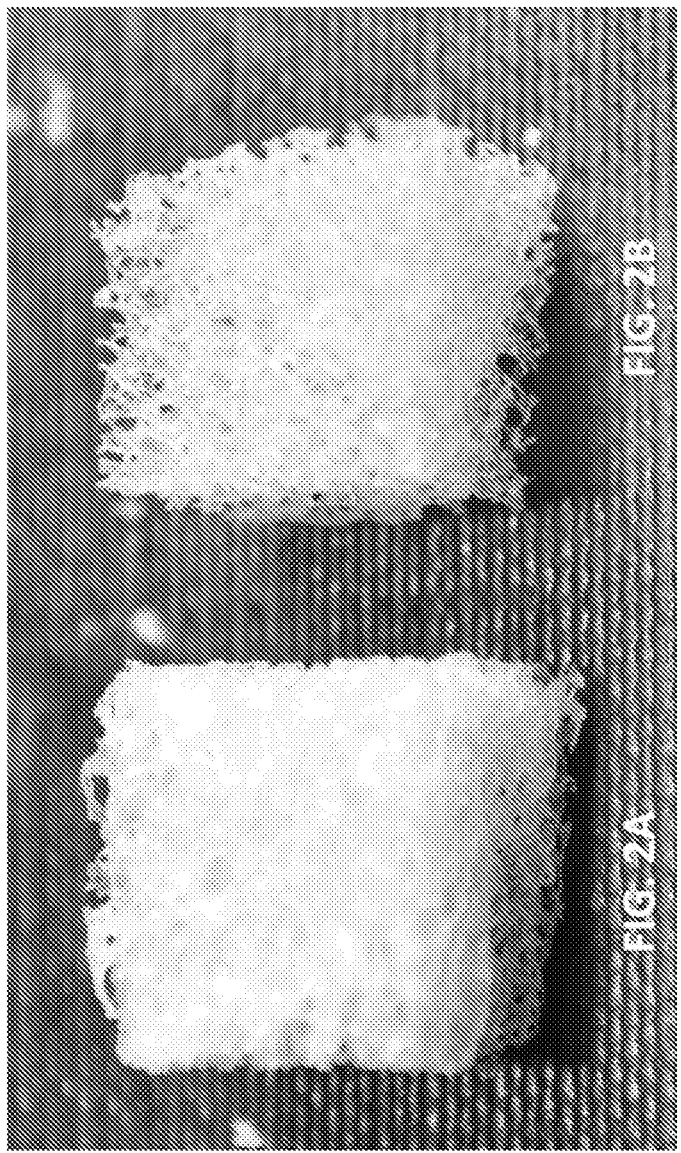

COMPOSITIONS OF AND METHODS FOR CANCELLOUS BONE MATRIX

CROSS-REFERENCE TO RELATED APPLICATION(S)

This application is a National Phase Patent Application and claims priority of International Patent Application Number PCT/US2014/024961, filed Mar. 12, 2014, which claims priority of US Patent Provisional Patent Application Nos. 61/801,766, filed Mar. 15, 2013, 61/814,197, filed Apr. 19, 2013, and 61/877,825, filed on Sep. 13, 2013, the entire content of which are incorporated herein by reference.

BACKGROUND

Bone grafts are commonly required to treat defects in the skeletal system caused by injury, disease or other defects. Defects often require such grafts to maintain space and provide a matrix for healing. The properties of the graft must support the healing response that is due to various mechanisms of bone healing known as osteoconduction, osteoinduction and osteogenesis. Osteoconduction is the ability of the graft to act as a matrix to support bone formation imitated by bone forming cells. Osteoinduction is a result of bone growth factors that stimulate differentiation of local cells to become bone forming cells, i.e. osteoblasts. Bone morphogenic proteins (BMP's) that are naturally occurring in bone, or that may be produced by recombinant gene technologies are responsible for osteoinduction. Osteogenesis refers to the ability of cells to directly form bone at the site of implantation due to normal physiological processes. These cells may be either resident at the graft site or transplanted to the site by autogenous bone, bone marrow aspirate, and/or implanted cells. There is a need for bone grafts to have osteoconductive, osteogenic and osteoinductive properties to support bone formation and healing.

SUMMARY

In embodiments of the present invention, a bone repair composition includes a cancellous bone matrix and demineralized bone particles. In some embodiments the bone repair composition further includes an excipient. Examples of an excipient include glycerol, ethanol, lecithin, sucrose, and combinations thereof.

In some embodiments of the present invention, the bone repair composition may also include an additive selected from bone marrow cells, mesenchymal stem cells, oxygenating materials (i.e., oxygen carrying materials), oxygen generating compounds, growth factors, antibiotics, antineoplastic agents, or combinations thereof. In some embodiments, the bone repair composition includes oxygenating materials such as a perflurocarbon. In some embodiments, the repair composition includes oxygen generating compounds such as peroxides (e.g., hydrogen peroxide, calcium peroxide), perchlorates (e.g., sodium perchlorate, potassium perchlorate) percarbonates (e.g., sodium percarbonate), or perborates (e.g., sodium perborate).

In some embodiments of the present invention, the demineralized bone particles of the bone repair composition are dispersed within the cancellous bone matrix. In some embodiments the cancellous bone matrix is demineralized. In some embodiments, the bone particles are demineralized cortical bone. In other embodiments, the demineralized bone particles are a mixture of cortical bone and cancellous bone.

In some embodiments of the present invention, the demineralized bone particles of the bone repair composition are uniformly dispersed throughout the cancellous bone matrix. In other embodiments, the demineralized bone particles of the bone repair composition are non-uniformly dispersed throughout the cancellous bone matrix such that a region around the edges of the cancellous bone matrix are free of bone particles.

In some embodiments of the present invention, the demineralized bone particles of the bone repair composition are disc-shaped or rod-shaped, or are fibers, or combinations thereof.

In some embodiments of the present invention, the outer edges of the cancellous matrix of the bone repair composition are coated with a material to retain the bone particles.

In some embodiments of the present invention, the bone repair composition includes an excipient infused within the matrix to render it flexible.

In some embodiments of the present invention, a method of making a bone repair composition includes hydrating dehydrated cancellous bone matrix to form a swollen cancellous bone matrix, loading a demineralized bone particle suspension into the swollen cancellous bone matrix to form a loaded cancellous bone matrix, and dehydrating the loaded cancellous bone matrix to form a bone repair composition including a cancellous bone matrix with demineralized bone particles therein. In some embodiments, the demineralized cortical bone particles are suspended in a hypertonic solution and loaded into the cancellous bone matrix in this hypertonic solution. In some embodiments, water is removed from the loaded cancellous bone matrix and then a hypotonic solution is loaded into the particle-loaded matrix to swell the demineralized cortical bone particles, thereby effectively securing the demineralized cortical bone particles within the cancellous bone matrix.

In one embodiment of the present invention the cancellous bone matrix is impregnated with demineralized fibers configured to bind to the cancellous bone matrix. The demineralized fibers have the advantage that they can be more tightly bound.

In one embodiment of the present invention the cancellous bone matrix is impregnated with a combination of crushed cortical bone and cancellous bone in the form of powder. The use of both cortical and cancellous bone utilizes more of the donated tissue.

In one embodiment of the present invention a coating is applied around the cancellous bone matrix to contain the DBM powder, so that the DBM powder is not directly bound but is "contained". This containment by means of a coating has the advantage of increasing the total content of DBM powder in the cancellous bone matrix because otherwise any non-bound DBM powder would fall out. Various biocompatible water soluble or biodegradable materials may be used, such as, but not limited to gelatin, collagen, polyvinyl alcohol, hyaluronic acid and other water soluble polymers.

In some embodiments the cancellous bone matrix may be completely filled with demineralized cortical powder/particulate and/or demineralized cancellous powder/particulate. In other embodiments, areas of the cancellous matrix are unfilled in order to facilitate the addition of further components intraoperatively. These additional components may include bone marrow aspirate or morcellized bone from the patient, cells, growth factors or other exogenous factors. By not fully impregnating the cancellous matrix, usage of the powder/particulate component is reduced, thereby reducing waste and cost and effectively using scarce donated tissue. For example; if a 1 cm×1 cm×1 cm cancellous bone matrix cube is filled with DBM powder and the surrounding 1 mm of space on all six sides of the cube is evacuated of DBM powder by shaking the powder out, by other means, then approximately 75% of the cube at the innermost extremes is impregnated, while approximately 1 mm on the outside remains available for facilitating infusion of bone marrow aspirate or other preferred materials to enhance bone growth. The cancellous bone matrix cube is often compressed before insertion into a bone void and allowed to refill into the available space. The surfaces of bone in contact with the inserted cube are rich in osteogenic and osteoinductive components. These would be in contact with the cube and easily infuse into the outer areas that are void of DBM powder. As such, these outer regions of the cancellous bone matrix cube have a high osteogenic potential without the presence of the DBM powder.

In some embodiments of the present invention, a kit for bone repair includes a cancellous bone matrix, demineralized bone particles, and saline. Additionally the kit may contain devices to facilitate preparation of the graft prior to implantation or to facilitate placement into the implant site.

BRIEF DESCRIPTION OF THE DRAWINGS

FIG. 1A is a photograph of demineralized cancellous bone with demineralized cortical powder (DCP), according to embodiments of the present invention.

FIG. 1B is a photograph of demineralized cancellous bone without DCP.

FIG. 2A is a photograph showing a closer view of the demineralized cancellous bone with DCP of FIG. 1A, according to embodiments of the present invention.

FIG. 2B is a photograph showing a closer view of the demineralized cancellous bone without DCP of FIG. 1B, according to embodiments of the present invention.

DETAILED DESCRIPTION

As used herein, cortical bone is dense bone that forms the shafts and surface layers of metaphyseal regions as well as the surface layer of flat bones, e.g. iliac crest. Cortical bone is dense with ≤10% porosity. The porosity of cortical bone may be formed by vascular channels (Volksmann's and Haversian canals), lacunae where bone cells within the matrix reside, and/or canaliculi which provide a channel for nutritional transport and cell to cell communication. As used herein, cancellous bone, also known as 'spongiosa,' has a macroporous architecture resembling a sponge. Cancellous bone is much less dense than cortical bone with the void space of cancellous bone being approximately 50% or greater. The porosity of cancellous bone depends on several factors, including anatomical location, i.e., cancellous bone is more dense just below joint surfaces and becomes more porous further from the joint. Other factors including metabolic state of the individual also influence porosity of cancellous bone.

The term demineralized bone is used to describe a process where acid (e.g. 0.6N HCl) or chelators (e.g. EDTA [ethylenediamine tetra-acetic acid]) is used to remove mineral from the bone. As used herein the term demineralizing refers to a process where acid or a chelator is used to remove mineral from the bone. The decrease in the amount of calcium in the bone determines the amount of demineralization. That is, completely demineralized bone has no calcium, or only trace amounts of calcium. In some embodiments completely demineralized bone has no more than 10% calcium. Any suitable acid or chelating agent may be used. An example of a suitable acid is 0.6N HCl. An example of a suitable chelating agent is EDTA. By reducing the pH to the level where bone mineral becomes soluble, the mineral component can be leached from the bone, leaving behind primarily type 1 collagen, as well as other components of bone, including growth factors that can influence bone healing by a process known as osteoinduction.

Both cortical bone and cancellous bone may be demineralized. Both demineralized cortical bone and demineralized cancellous bone may be in the form of a powder or particulate or segments where the native three-dimensional architecture is maintained. As used herein, powder and particulate are used to describe cortical and/or cancellous bone that has been ground, pulverized, or shredded, into granules, a powder, or elongate particles (fibers) or other shapes of various sizes.

As used herein, cancellous bone that maintains its natural three-dimensional architecture and porosity is referred to as cancellous bone matrix. Cancellous bone that has been ground, etc. is referred to as cancellous powder or cancellous particulate. Demineralized cancellous bone that has been ground, etc., is also referred to as DBM (Demineralized Bone Matrix) or DBM powder or Demineralized Cancellous Powder (DCP) or demineralized bone fibers.

As used herein, demineralized cortical bone is referred to as demineralized bone matrix (DBM), DBM powder or Demineralized Cortical Powder.

In some embodiments of the present invention, a bone repair composition for treating defects of bones includes a mineralized or demineralized cancellous bone matrix and demineralized cortical bone, demineralized cancellous bone, or demineralized cortical and cancellous bone all derived from allogeneic (human) or xenogeneic (animal) sources. The combination of cancellous bone matrix and demineralized cortical and/or demineralized cancellous particulate bone provides a product that has the advantages of cancellous bone matrix having a higher overall density of bone compared to cancellous bone which is not impregnated. Thus the combination includes a higher proportion of osteoinductive proteins. The use of demineralized cortical bone powder together with cancellous bone yields a product incorporating the advantages found in each of the cancellous bone and the demineralized cortical bone. That is, cancellous bone has an interconnected, highly porous structure that provides an excellent matrix architecture for the formation of new bone, i.e., it is highly osteoconductive. To complement the cancellous bone, demineralized bone particles having only cortical bone, or a high proportion of cortical bone, are highly osteoinductive. The osteoinductive proteins (e.g., bone morphogenic proteins (BMPs)) that are 'unmasked' by the removal of the hydroxyapatite mineral component are capable of guiding the differentiation of uncommitted cells at the site of implant into bone forming cells. Containment of these osteoinductive agents within a cancellous bone matrix that is highly osteoconductive allows for efficacious bone formation. The combination of these properties provides for a bone repair composition having improved utility for bone growth.

In some embodiments of the present invention, the cancellous bone of the cancellous bone matrix is not demineralized and the bone particles are demineralized. This provides a graft with structural integrity due to the mineralized bone of the cancellous matrix. The use of demineralized bone particles provides materials where the mineralized matrix is removed thus exposing the bone morphogenic proteins of the bone to provide an osteoinductive material.

The combination of these properties provides for a bone repair composition having improved utility for bone growth.

In some embodiments, the present repair composition of the present invention may include additional additives selected to enhance the handling properties and bone healing performance of the constructs. Selected additives are added to the bone repair composition to improve physical and/or physiological effects. In some embodiments, an additive is selected to hydrate the cancellous bone matrix to maintain "sponginess" in the absence of water. An example of a hydrating additive includes glycerol. In some embodiments, an additive is selected to improve the bone growth effect or other physiological effects of the bone repair composition. For example, a selected additive may include perfluorocarbons (PFCs) and/or other oxygen-generating compounds in order to enhance the ability of the cells within the cancellous bone matrix to form bone. In other examples, selected additives to promote bone growth and healing include growth factors, cells with bone forming potential and/or immune modulatory potential e.g. mesenchymal stem cells MSCs, or bone marrow cells, antibiotics, anti-neoplastic agents, oxygenating materials, and combinations thereof. In some embodiments, an additive is selected to inhibit microbial growth. For example, a selected additive may be gentamicin. Non-limiting examples of additives to enhance bone growth include growth factors such as bone morphogenetic proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-$\beta$s), including TGF-$\beta$-1, TGF-$\beta$.-2, and TGF-$\beta$.-3, and inhibitors for tumor necrosis factor (e.g., anti-TNF-$\alpha$). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, the entire contents of which are incorporated herein by reference. The polynucleotides encoding the same may also be administered as gene therapy agents. The preferred bioactive substances are the recombinant human bone morphogenetic proteins (rhBMPs) because they are available in relatively unlimited supply and do not transmit infectious diseases. In some embodiments, the bone morphogenetic protein is a rhBMP-2, rhBMP-4, rhBMP-7, or heterodimers thereof BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al., the entire contents of all of which are herein incorporated by reference.

In some embodiments, selected additives include those that improve physical handling properties, e.g., plasticizers, binders, adhesives, wetting agents, and surfactants.

In some embodiments, a biocompatible material is included to enhance the osteogenic properties of the bone implant. The addition and selection of at least one biocompatible material may depend on the size of the bone graft site and the location of the site. A broad range of biocompatible materials are available, including: collagen and insoluble collagen derivatives, hydroxyapatite, tricalcium phosphate, and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, magainins, peptides, vitamins, inorganic elements, co-factors for protein synthesis; hormones; endocrine tissue or tissue fragments; synthesizers; enzymes such as collagenase, peptidases, and oxidases; polymer cell scaffolds with parenchymal cells; surface cell antigen eliminators; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; nucleic acids; and, bioerodable polymers such as those disclosed in U.S. Pat. Nos. 4,764,364 and 4,765,973 and European Patent Application 168,277. The amounts of such optionally added substances can vary widely with optimum levels being readily determined by those having ordinary skill in the art.

In one embodiment of the present invention the cancellous bone matrix is impregnated with demineralized fibers configured to be contained within the cancellous bone matrix. The demineralized fibers have the advantage that they can be more easily contained within the cancellous bone matrix. That is, the demineralized cortical and/or cancellous bone fibers may have more than one point of contact within a pore or the pores of the cancellous bone matrix. The demineralized fibers have the advantage that most of the fibers provided to the cancellous bone matrix are able to be contained, thereby providing demineralized bone powder/particulate more consistently to the cancellous bone matrix for increased reproducibility and quality of the cancellous bone and demineralized bone particulate/powder composition. In some embodiments of the present invention, the combination of demineralized particulates and fibers may be utilized; the particulates may be able to reach areas within the cancellous bone matrix where the fibers cannot, while the fibers provide an enhanced ability to resist removal from the matrix.

In one embodiment of the present invention, the cancellous bone matrix is impregnated with a combination of crushed cortical bone and cancellous bone in the form of powder. This combination of cortical bone and cancellous bone has the advantage of utilizing more donated tissue.

In one embodiment of the present invention, a coating is applied around the cancellous cube to contain the DBM powder, so that it is "contained". This coating may allow an increased content of DBM powder by preventing any non-bound DBM powder from falling out. Various water-soluble or degradable materials may be used, such as, but not limited to gelatin, collagen, polyvinyl alcohol, polyacrylic acid, polyacrylamide, polyethylene glycol, polyethylene-propylene glycol, dextran, xanthum gum, carrageenan, carboxymethyl cellulose, hyaluronic acid.

In some embodiments the cancellous bone matrix may be completely filled with demineralized cortical and/or cancellous powder/particulate, thereby having uniformly dispersed powder/particulate. In other embodiments, some areas of the cancellous bone matrix are left unfilled to facilitate addition of further components intraoperatively, and thereby having non-uniformly dispersed powder/particulate. These may include bone marrow aspirate or morcellized bone from the patient, cells, growth factors or other exogenous factors. By not fully impregnating the cancellous bone matrix, the amount of the bone powder/particulate component is reduced which avoids waste and saves cost and donated tissue. For example, a 1 cm×1 cm×1 cm cancellous bone matrix cube is filled with DBM powder and then the surrounding 1 mm of space on all six sides of the cube is evacuated of DBM powder by shaking the powder out, by other means, resulting in approximately 75% of the cube at the innermost extremes being impregnated, while just 1 mm on the outside remains available for facilitating infusion of bone marrow aspirate or other preferred materials to enhance bone growth. In some embodiments, the cancellous bone matrix cube is compressed before insertion into a bone void and allowed to refill into the available space. The surfaces of the patient's bone in contact with the inserted cube are rich in osteogenic and osteoinductive components. These would be in contact with the cube and easily infuse into the outer areas that are specifically voided of DBM powder. As such, these outer regions have a high osteogenic potential without the presence of the DBM powder.

While it is a benefit in the utilization of less DBM powder—saving cost and donated tissue, the availability of "open" areas, especially near the periphery of the cancellous bone matrix increases the ability to absorb these components and allows for comparable or improved results.

Moreover, the bone repair compositions of the present invention have at least the following characteristics: 1) easy to handle during the surgical procedure; 2) enhanced bone forming capability due the DBM powder, 3) enhanced bone forming capability due to the oxygen transport and selected additives also disclosed herein; and 3) biocompatible and easily mixed with ancillary constituents commonly used during grafting procedures, e.g., autograft bone and bone marrow aspirate.

In some embodiments of the present invention, the bone graft composition includes an excipient to facilitate the loading and retention of particulates into the cancellous bone matrix. In some embodiments, the particulates include demineralized cortical bone powder/particulate, demineralized cancellous bone powder/particulate or combinations thereof. With suspension of demineralized bone powder/particulate in an excipient, the cortical or mixture of cortical and cancellous bone powder can be effectively incorporated into the cancellous bone matrix. In some embodiments, an excipient for loading the particulates into the cancellous bone matrix is an excipient solution. Non-limiting examples of excipient solutions for loading and retention of particulates include glycerol, alcohols, hypertonic solutions, wetting agents, and combinations thereof. Additional non-limiting examples of excipients include phosphatidyl choline, p. inositol, phospholipids, hydroxymethyl cellulose, hyaluronic acid, polyvinyl alcohol, and fatty acids. A non-limiting example of a fatty acid includes omega-3 fatty acids.

Of the possible excipient solutions, hypertonic solutions cause the cortical bone particles to shrink, which may be desired for loading the particles into the cancellous bone matrix. In some embodiments, after loading of the smaller particles, the cancellous bone matrix is then dehydrated to remove the water from the hypertonic solution. The cortical bone particles in the cancellous bone matrix are then enlarged (i.e. swollen) by the addition of a hypotonic or isotonic solution that acts as a 'swelling agent.' In this way, the shrunken particles that have already been introduced into the pores of the cancellous bone matrix are then swollen, thereby effectively "locking" or securing the particles into the pores of the matrix. Non-limiting examples of swelling agents include glycerol, lecithin and wetting agents (e.g., surfactants). Non-limiting examples of surfactants include polyoxymers, Pluronic® F68, Pluronic® F127, Triton™ X-100, and Tween®-20.

In particular, useful polyhydroxy swelling agents possess from 2 up to 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives thereof Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamnose, inositol, fructose, galactose, glucose, mannose, sorbose, sucrose, maltose, lactose, maltitol, lactitol, stachyose, maltopentaose, cyclomaltohexaose, trehalose, carrageenan, agar, alginic acid, guar gum, gum tragacanth, locust bean gum, gum arabic, xanthan gum, amylose, mixtures and copolymers thereof.

In some embodiments, demineralized cortical and/or cancellous bone powder/particulate is suspended in a glycerol and water solution, and this particulate suspension is then loaded into a demineralized cancellous bone matrix graft. The vapor point of glycerol is much higher than water, so the water is easily removed, leaving behind the glycerol to maintain the spongy character of the demineralized cancellous matrix. Glycerol is also extremely hydroscopic, such that water, saline, blood, bone marrow aspirate or similar aqueous liquids are readily imbibed, allowing for excellent handling characteristics during surgery. As such, once the particulate has been introduced into the cancellous bone matrix using an excipient, the particulate may then be encapsulated within the cancellous bone matrix by removing the swelling/shrinking agents. This approach is an example of incorporating the particles into the porous three-dimensional structure of the cancellous bone matrix, and subsequently holding them in place such that the particles are not removed during handling prior to or during surgical procedures. In other embodiments, other agents may be used to hold the particles in place by means of electrostatic charge and/or surface attraction.

The size of the cancellous graft can range from a few millimeters to several centimeters depending on the intended procedure. Anatomical constraints limit the upper range of sizes. Cancellous bone from allogeneic sources (human donors) is limited by the size of the femur and tibial metaphyses, whereas bone from other species such as bovine bone has larger potential sizes. The graft may be used in the form of a monolithic implant or may be granules formed from the enhanced cancellous bone matrix.

In some embodiments the size of demineralized bone particles is matched to the size of the cancellous matrix pores. Demineralized cortical and/or demineralized cancellous bone particles are produced by conventional means and then size selected and classified by sieving. The cancellous bone matrix pore size is estimated by measuring with calipers or from a microscope image and then particles selected to fit snuggly into the pores. The bone particles are then impregnated or dispersed into the cancellous matrix by various means described elsewhere in this disclosure.

In some embodiments particles of demineralized bone are designed such that once impregnated into the pores of the matrix, they are not easily dislodged. Particles with a high surface area ratio such as discs and elongate fibers have a greater contact surface within the cancellous matrix pores resulting in them being more tightly bound and less prone to dislodgement.

In other embodiments, once demineralized bone particles are impregnated into a cancellous bone matrix the construct is impregnated with a solution of a polymer to enhance the binding of the bone particulates to the cancellous bone matrix. Suitable binding materials include trehalose, lecithin, as well as collagen that has been treated to have a sticky consistency, thus binding the particles within the matrix. Such a collagen preparation can be produced by heating bone collagen in an acid solution, as is described by O'Leary and Prewett in U.S. Pat. No. 5,236,633, the entire contents of which are herein incorporated by reference.

In some embodiments the demineralized particles are impregnated or dispersed into the central regions of the cancellous bone matrix, but not in the periphery of the cancellous bone matrix. As described in this disclosure, various means may be used to adhere the particles. This allows for areas within the cancellous bone matrix to be available for incorporation of bone marrow aspirate, morcellized bone from the patient or other materials into the pores of the matrix without dislodging the impregnated particles and has advantages in that less particulate material is required resulting in cost savings and avoiding wasting donor tissue.

In some embodiments the demineralized particles are injected into the central regions of the cancellous bone matrix using a syringe and needle type of approach. This allows for controlled placement of the particulate within the cancellous matrix. This method may also be used intraoperatively where the particulate is mixed with bone marrow aspirate and then infused into the graft at the time of use.

In various embodiments, after impregnating cancellous bone matrix with demineralized particles, a heating step is performed where the construct is heated to an elevated temperature between about 40° C. and about 70° C. degrees while in a hydrated state for a period of about 30 minutes up to about 24 hours. These conditions result in alterations in the collagen within bone that cause it to adhere to other particles and the surface of the matrix.

In one aspect of the invention the cancellous matrix and demineralized bone powder are provided in a kit. At the time of the procedure the bone particles are suspended in a liquid and infused into the matrix.

The bone particles may be suspended in saline, bone marrow aspirate or a perfluorocarbon. Suitable perfluorocarbons include perfluorodecalin, perfluorohexane, perfluorotributylamine, or perfluoroperhydrophenanthrene. Perfluorocarbons have a high oxygen solubility and act as reservoirs of oxygen. The use of perfluorocarbons has been shown to be advantageous to bone repair.

To further enhance the oxygen content of the device beyond that achieved through the use of an additive with an high oxygen solubility such as a perfluorocarbon (PFC), in some embodiments additional additives to the matrix include oxygen generators. The oxygen generating compounds also pose challenges to maintain them in a formulation where they do not react and release the oxygen prematurely. Suitable oxygen generators include peroxides (e.g., hydrogen peroxide, calcium peroxide, magnesium peroxide), perchlorates (e.g., sodium perchlorate, potassium perchlorate) percarbonates (e.g., sodium percarbonate), or perborates (e.g., sodium perborate).

In some embodiments, the kit includes separate syringes to contain the cancellous matrix and bone particles and may be connected to allow the suspension to be infused into the matrix. Furthermore, the syringe containing the matrix imparts a reduced pressure, effected by pulling the plunger back on that syringe or on a conjoined syringe.

In some embodiments the kit includes syringe and needles for harvesting of the patient's bone marrow.

The following Examples of the bone repair composition are presented for illustrative purposes only, and do not limit the scope or content of the present application.

EXAMPLES

Example 1

Rehydration of Cancellous Bone Matrix

A demineralized and dehydrated (freeze-dried) cancellous bone matrix cube ("cube") approximately 1 $cm^3$ in size was supplied by Bacterin International Holdings, Inc. The cube was placed into a solution of 35% glycerol in water. The cube was soaked in the glycerol solution for approximately one hour, at which point the cube was rehydrated—i.e., it was compressible and spongy, as opposed to the stiffness and brittleness of the bone cube before rehydration. The rehydrated cube was removed from the glycerol solution, blotted dry and placed into a vacuum oven to remove any additional moisture (FIGS. 1B, 2B). After removal of moisture, the cube remained pliable due to the residual glycerol.

Example 2

Influence of 70% ethanol and glycerol on volume of demineralized cortical powder (DCP)

DCP was placed into a vial filling to the 4 cc mark. 70% ethanol was then added to the 10 cc mark. After incubating for 1 hour at room temperature, the vial was centrifuged at 500 rpm for 30 seconds. The DCP was at the 5 cc mark. The fluid was decanted and replaced by water, then centrifuged as above. This was repeated twice. The DCP was fully rehydrated and now the powder level was at 5.6 cc in the vial demonstrating approximately 10% swelling by use of the 70% ethanol. The water was then decanted and 2 cc of glycerol added, then additional water to the 10 cc mark. After shaking to mix and centrifuging as above, the powder level was now at 6 cc. This demonstrated the DCP had swollen approximately 20% compared to the 70% ethanol solution and 10% compared to water. This experiment demonstrates feasibility to cause swelling of DCP by controlling the solution it is rehydrated in.

Example 3

Loading of DCP/Glycerol into Cancellous Bone Matrix

Demineralized cortical powder (DCP) was prepared as follows: 1.21 grams of DCP (from AlloSource®) was placed into a vial and 6.02 gm of a 50% glycerol/water solution was added. The mixture was shaken and allowed to incubate at room temperature in a sealed vial for 24 hours. Again, swelling was noted as in Example 2 above. This mixture was then placed into a syringe with its end removed such that it was a cylinder with a plunger, and the mixture of DCP was forced into the cube by placing the tip onto the cube and compressing the cube flat. As the mixture was expelled onto the cube, the downward force on the cube was slowly reduced, to allow it to return to its normal shape, with the DCP loaded inside the pore spaces (FIGS. 1A, 1B). After removal of moisture, the cube remained pliable due to the residual glycerol.

Example 4

Loading of DCP/Ethanol into Cancellous Sponge

A demineralized and dehydrated cancellous bone matrix cube (Bacterin, supra) was placed in a 70% ethanol and water solution without a glycerol rehydration step as described in Example 1. DCP was suspended in a 70% ethanol solution. The DCP suspension did not result in rehydration and swelling of the powder, but instead the DCP particle size remained small. The DCP solution was then introduced into the cube using the same syringe as described above, but injecting it by forcing it into the matrix of the uncompressed cube. The resulting construct was then placed into a vacuum oven to remove the water and ethanol, leaving the dried DCP within the matrix. The result was a demineralized cancellous bone matrix cube (DCC) loaded with DCP in the internal architecture.

Example 5

Glycerol Rehydration of DCP/Ethanol-Loaded Cancellous Bone Matrix

The DCP-loaded cancellous bone matrix from Example 3 was placed into a 35% glycerol solution followed by rehydration for 1 hour, resulting in softening of the cancellous bone matrix and swelling of the loaded DCP therein. The glycerol solution induced swelling and enlargement of the DCP particles, and secured the DCP in place within the cancellous bone matrix. This glycerol and DCP-loaded cancellous bone matrix was placed into a vacuum oven to remove the water, leaving behind the glycerol which maintained hydration of the cancellous bone matrix such that it was compressible. The glycerol further provided 'stickiness' which helped retain the DCP in the cancellous bone matrix.

Example 6

Lecithin Rehydration of DCP/Ethanol-Loaded Cancellous Sponge

The DCP-loaded cancellous sponge from Example 3 was placed into a 10% lecithin solution followed by rehydration for 1 hour, resulting in softening of the cube and swelling of the loaded DCP therein. The lecithin solution induced swelling and enlargement of the DCP particles, and secured the DCP in place within the sponge matrix. This lecithin and DCP-loaded sponge cube was placed into a vacuum oven to remove the water, leaving behind the lecithin which maintained hydration of the construct such that it was compressible. The lecithin further provided 'stickiness' which helped retain the DCP in the sponge matrix. This example demonstrates that swelling agents other than glycerol are effective at increasing the volume of DCP.

Example 7

Sucrose/Glycerol Rehydration of DCP/Ethanol-Loaded Cancellous Sponge

The DCP-loaded cancellous sponge from Example 3 was placed into a 10% sucrose and 25% glycerol in water solution for 1 hour. This sucrose/glycerol and DCP-loaded sponge cube was then placed into a vacuum oven to remove the water, leaving behind the sucrose and glycerol. The sucrose appeared to provide additional binding and "stickiness" to retain and "lock" the DCP particulates within the cancellous bone sponge.

Example 8

Saline/Glycerol Rehydrated Cancellous Sponge Loaded with DCP in Ethanol and then Swollen with Glycerol Demineralized cancellous cubes were hydrated with saline (0.9% NaCl) in a 35% glycerol solution, resulting in swelling of the cancellous cube. DCP was suspended in 70% ethanol as described in Example 2. The DCP was introduced into the cancellous matrix using the syringe technique described above in Example 3. The resulting DCP-loaded cancellous cube was then soaked in 35% glycerol, resulting in swelling of the DCP such that it was held securely within the matrix. The swelling the DCP in place and the 'stickiness' of the glycerol acting as a binding agent were observed.

Example 9

Particle Sizes of DBM Powder

DBM powder from cortical and cancellous bone was prepared in a range of particle sizes from 100 microns to 4 mm using standard techniques for grinding and sieving. The powder was then selected to match the natural pore structure of the cancellous sponge as pore size varies with the anatomical location from where it is obtained. Subchondral (just below the joint surface) cancellous tends to be very dense with small pores, whereas cancellous further from the joint surface has larger pores. By matching the particle size of the powder to the pore size of the cancellous matrix, i.e. large particle impregnated into large pores and vice versa, the powder appeared to be more resistant to subsequent dislodging during rehydration.

Example 10

Loading of Additive to Cancellous Sponge

An additive may also be incorporated into the cancellous bone sponge directly in its own suspension added by syringe as disclosed, or in suspension together with DBM powder as described herein. For example, an additive such as a perfluorocarbon may be added together with the DBM powder. A cancellous cube with DBM powder prepared according to the methodology of Example 4 was subsequently placed in a container of Perfluorotributylamine (PFTBA). The cubes of material were removed and blotted dry. The uptake of PFTBA ranged from 0.5 to 1.0 g/cm$^3$.

Example 11

Preparation of Granular Product

The cancellous bone infused with DBM powder according to the methodology of Example 4 was rough chopped to form granules <4 mm in dimension.

Example 12

PFTBA Cancellous Bone Matrix

DCP was placed into a vial along with lecithin, Pluronic® F68 and PFTBA to form a slurry. This slurry was then 'injected' into a demineralized cancellous sponge that had not been rehydrated. The resulting construct was then placed into a vacuum oven at 40° C. to remove any moisture. The resulting combination created a construct wherein the PFTBA and DCP were effectively integrated into the cancellous matrix providing the desirable graft with osteoconductive, osteoinductive, oxygen transport and handling properties.

Example 13

Cancellous Bone Matrix with Oxygen Generating Compound

A slurry as in Example 12 above further including calcium peroxide as an oxygen generating compound was created using the following ratios: 1 cc PFTBA, 1 cc 20% Pluronic® F68, 1 cc lecithin, 250 mg CaO$_2$ and DCP added to create a low viscosity slurry. The slurry was injected into the cancellous matrix as in Example 11, and then dried using vacuum oven at 40° C. The resulting construct was compressible. This approach of removing the water also resulted in the CaO$_2$ being stable as water is required for the oxygen releasing reaction to appreciably occur.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of making a monolithic bone implant composition, comprising:
    hydrating a cancellous bone matrix to form a swollen cancellous bone matrix;
    loading demineralized bone particles into the swollen cancellous bone matrix to form a loaded cancellous bone matrix; and
    dehydrating the loaded cancellous bone matrix to form a monolithic bone implant composition comprising a cancellous bone matrix with demineralized bone particles therein.

2. The method of claim 1, wherein the hydrating comprises a solution selected from the group consisting of water, saline, glycerol, lecithin, sucrose, and combinations thereof.

3. The method of claim 1, wherein the demineralized bone particles comprise demineralized bone particles in a solution selected from the group consisting of water, saline, alcohol, glycerol, and combinations thereof.

4. The method of claim 1, wherein the dehydrating comprises heating the loaded cancellous bone matrix at a temperature in a range from about 40° C. to about 75° C.

5. The method of claim 1, wherein the dehydrating comprises applying a vacuum or reduced pressure and/or heating to the loaded cancellous bone matrix.

6. The method of claim 1, wherein the demineralized bone particles comprise ethanol.

7. The method of claim 1, further comprising loading a hypotonic solution into the loaded cancellous bone matrix to swell the demineralized bone particles.

8. The method of claim 1, further comprising loading an additive into the swollen cancellous bone matrix.

9. The method of claim 1, wherein the demineralized bone particles comprise an additive.

10. The method of claim 9, wherein the additive is selected from the group consisting of bone marrow cells, mesenchymal stem cells, oxygenating materials, growth factors, antibiotics, anti-neoplastic agents, and combinations thereof.

11. The method of claim 1, wherein the hydrating comprises rehydrating a dehydrated cancellous bone matrix.

12. A monolithic bone implant composition made by the method of claim 1.

* * * * *